(12) United States Patent
Thomas et al.

(10) Patent No.: US 10,123,870 B2
(45) Date of Patent: Nov. 13, 2018

(54) ALIGNMENT OF AN IMPLANTABLE MEDICAL DEVICE

(71) Applicant: St. Jude Medical, Cardiology Division, Inc., St. Paul, MN (US)

(72) Inventors: Ralph Joseph Thomas, Champlin, MN (US); Aaron J. Chalekian, Savage, MN (US); Gary W. Geiger, Fridley, MN (US); Peter J. Ness, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 598 days.

(21) Appl. No.: 14/445,848

(22) Filed: Jul. 29, 2014

(65) Prior Publication Data

US 2015/0073538 A1    Mar. 12, 2015

Related U.S. Application Data

(60) Provisional application No. 61/877,107, filed on Sep. 12, 2013.

(51) Int. Cl.
*A61F 2/24* (2006.01)
*A61M 25/01* (2006.01)
*A61F 2/962* (2013.01)
*A61F 2/966* (2013.01)
*A61B 17/34* (2006.01)
*A61M 25/02* (2006.01)

(52) U.S. Cl.
CPC .......... *A61F 2/2427* (2013.01); *A61F 2/2418* (2013.01); *A61F 2/2433* (2013.01);
(Continued)

(58) Field of Classification Search
CPC .......... A61F 2/01; A61F 2/013; A61F 2/2427; A61F 2/243; A61F 2/2433; A61F 2/2436;
(Continued)

(56) References Cited

U.S. PATENT DOCUMENTS 3,384,088 A   5/1968   Miseo
3,657,744 A   4/1972   Ersek
(Continued)

FOREIGN PATENT DOCUMENTS

EP   1129744 A1   9/2001
EP   1157673 A2   11/2001
(Continued)

OTHER PUBLICATIONS

"Adjacent." Merriam-Webster.com. Merriam-Webster, n.d. Web. Aug. 20, 2017.*
(Continued)

*Primary Examiner* — Katrina Stransky
*Assistant Examiner* — Kankindi Rwego
(74) *Attorney, Agent, or Firm* — Lerner, David, Littenberg, Krumholz & Mentlik, LLP

(57) ABSTRACT

A transcatheter valve delivery system includes a longitudinal member extending between a proximal end and a distal end, and having a compartment adjacent the distal end for holding a medical device in a collapsed condition. An alignment element is connected to the longitudinal member and is movable relative to the longitudinal member between a stowed position and a deployed position. In the deployed position, the alignment element is configured to urge against an anatomical surface to position the longitudinal member at a desired location relative to the anatomical surface.

5 Claims, 16 Drawing Sheets

(52) U.S. Cl.
CPC .......... *A61F 2/2436* (2013.01); *A61F 2/2439* (2013.01); *A61M 25/0147* (2013.01); *A61M 25/02* (2013.01); *A61B 2017/3484* (2013.01); *A61F 2/962* (2013.01); *A61F 2/966* (2013.01); *A61F 2210/0014* (2013.01); *A61F 2220/0025* (2013.01); *A61M 2025/0293* (2013.01)

(58) Field of Classification Search
CPC .......... A61F 2/2439; A61F 2/848; A61F 2/95; A61F 2/962; A61F 2/966; A61F 2002/011; A61F 2002/015; A61F 2002/016; A61F 2002/018; A61F 2002/9505; A61F 2002/9511; A61F 2002/9517; A61F 2002/9522; A61F 2002/9528; A61F 2002/9534; A61F 2002/9665; A61F 2/954; A61M 25/04; A61M 2025/0063; A61M 25/01; A61M 25/0662; A61M 2025/01; A61M 2025/0293; A61M 2025/0681; A61M 2025/0687; A61M 25/0125; A61M 25/0152; A61M 25/0175; A61B 17/12022; A61B 17/12113
See application file for complete search history.

(56) References Cited

U.S. PATENT DOCUMENTS

| | | | |
|---|---|---|---|
| 3,724,238 A | 4/1973 | Retali et al. | |
| 4,423,730 A | 1/1984 | Gabbay | |
| 4,641,657 A | 2/1987 | Ellis | |
| 5,368,592 A | 11/1994 | Stern et al. | |
| 5,372,587 A | 12/1994 | Hammerslag et al. | |
| 5,405,344 A | 4/1995 | Williamson et al. | |
| 5,507,725 A | 4/1996 | Savage et al. | |
| 5,549,594 A | 8/1996 | Brunken | |
| 5,569,270 A | 10/1996 | Weng | |
| 5,575,799 A | 11/1996 | Bolanos et al. | |
| 5,749,881 A | 5/1998 | Sackier et al. | |
| 5,843,167 A | 12/1998 | Dwyer et al. | |
| 5,868,685 A | 2/1999 | Powell et al. | |
| 5,924,424 A | 7/1999 | Stevens et al. | |
| 5,928,260 A * | 7/1999 | Chin ............... | A61B 17/12022 604/107 |
| 5,968,068 A | 10/1999 | Dehdashtian et al. | |
| 6,077,297 A | 6/2000 | Robinson et al. | |
| 6,183,432 B1 | 2/2001 | Milo | |
| 6,306,141 B1 | 10/2001 | Jervis | |
| 6,464,684 B1 | 10/2002 | Galdonik | |
| 6,623,518 B2 | 9/2003 | Thompson et al. | |
| 6,743,239 B1 | 6/2004 | Kuehn et al. | |
| 6,814,746 B2 | 11/2004 | Thompson et al. | |
| 6,830,584 B1 | 12/2004 | Seguin | |
| 7,018,406 B2 | 3/2006 | Seguin et al. | |
| 7,300,431 B2 | 11/2007 | Dubrovsky | |
| 7,311,730 B2 | 12/2007 | Gabbay | |
| 7,510,572 B2 | 3/2009 | Gabbay | |
| 7,637,905 B2 | 12/2009 | Saadat et al. | |
| 7,682,390 B2 | 3/2010 | Seguin | |
| 7,803,185 B2 | 9/2010 | Gabbay | |
| 7,811,277 B2 | 10/2010 | Boulais | |
| 9,227,990 B2 | 1/2016 | Phull et al. | |
| 2003/0050694 A1 | 3/2003 | Yang et al. | |
| 2003/0233108 A1 | 12/2003 | Gellman et al. | |
| 2004/0210304 A1 | 10/2004 | Seguin et al. | |
| 2005/0137622 A1 | 6/2005 | Griffin | |
| 2005/0137695 A1 | 6/2005 | Salahieh et al. | |
| 2005/0137697 A1 | 6/2005 | Salahieh et al. | |
| 2005/0165352 A1 | 7/2005 | Henry et al. | |
| 2005/0177138 A1 | 8/2005 | Dubrovsky | |
| 2005/0222604 A1 | 10/2005 | Schaeffer | |
| 2006/0058872 A1 | 3/2006 | Salahieh et al. | |
| 2006/0074484 A1 | 4/2006 | Huber | |
| 2006/0100687 A1 | 5/2006 | Fahey et al. | |
| 2006/0106415 A1 | 5/2006 | Gabbay | |
| 2006/0142848 A1 | 6/2006 | Gabbay | |
| 2006/0167468 A1 | 7/2006 | Gabbay | |
| 2006/0235502 A1 | 10/2006 | Belluche et al. | |
| 2006/0259120 A1 | 11/2006 | Vongphakdy et al. | |
| 2007/0010876 A1 | 1/2007 | Salahieh et al. | |
| 2007/0027534 A1 | 2/2007 | Bergheim et al. | |
| 2007/0043259 A1 | 2/2007 | Jaffe et al. | |
| 2007/0043435 A1 | 2/2007 | Seguin et al. | |
| 2007/0055358 A1 | 3/2007 | Krolik et al. | |
| 2007/0073376 A1 | 3/2007 | Krolik et al. | |
| 2007/0073391 A1 | 3/2007 | Bourang et al. | |
| 2007/0088431 A1 | 4/2007 | Bourang et al. | |
| 2007/0112422 A1 | 5/2007 | Dehdashtian | |
| 2007/0123925 A1 * | 5/2007 | Benjamin ......... | A61M 25/0041 606/194 |
| 2007/0162100 A1 | 7/2007 | Gabbay | |
| 2007/0168013 A1 | 7/2007 | Douglas | |
| 2007/0203575 A1 | 8/2007 | Forster et al. | |
| 2007/0239271 A1 | 10/2007 | Nguyen | |
| 2007/0244552 A1 | 10/2007 | Salahieh et al. | |
| 2007/0250113 A1 | 10/2007 | Hegeman et al. | |
| 2008/0065122 A1 | 3/2008 | Stack et al. | |
| 2008/0071369 A1 | 3/2008 | Tuval et al. | |
| 2008/0147160 A1 | 6/2008 | Ghione et al. | |
| 2008/0147182 A1 | 6/2008 | Righini et al. | |
| 2008/0228223 A1 | 9/2008 | Alkhatib | |
| 2008/0319526 A1 * | 12/2008 | Hill ................ | A61F 2/2418 623/1.12 |
| 2009/0054975 A1 | 2/2009 | del Nido et al. | |
| 2009/0062606 A1 | 3/2009 | Ueda et al. | |
| 2009/0062839 A1 | 3/2009 | Kurrus | |
| 2010/0004740 A1 | 1/2010 | Seguin et al. | |
| 2010/0057000 A1 * | 3/2010 | Melsheimer ........ | A61M 25/04 604/103.03 |
| 2010/0204708 A1 | 8/2010 | Sharma | |
| 2010/0228152 A1 | 9/2010 | Fisher et al. | |
| 2010/0228191 A1 | 9/2010 | Alvarez et al. | |
| 2010/0286768 A1 | 11/2010 | Alkhatib | |
| 2010/0298931 A1 | 11/2010 | Quadri et al. | |
| 2011/0098800 A1 | 4/2011 | Braido et al. | |
| 2011/0207999 A1 | 8/2011 | Torisawa et al. | |
| 2011/0224678 A1 | 9/2011 | Gabbay | |
| 2011/0245917 A1 | 10/2011 | Savage et al. | |
| 2012/0078350 A1 | 3/2012 | Wang et al. | |
| 2012/0209375 A1 * | 8/2012 | Madrid ............... | A61F 2/2433 623/2.11 |
| 2012/0303111 A1 | 11/2012 | Dwork et al. | |
| 2013/0060328 A1 | 3/2013 | Rothstein | |
| 2013/0103047 A1 | 4/2013 | Steingisser et al. | |
| 2013/0274870 A1 | 10/2013 | Lombardi et al. | |
| 2013/0297012 A1 | 11/2013 | Willard | |
| 2013/0297102 A1 | 11/2013 | Hughes et al. | |

FOREIGN PATENT DOCUMENTS

| | | |
|---|---|---|
| EP | 1716822 A1 | 11/2006 |
| EP | 1926455 A2 | 6/2008 |
| FR | 2765098 A1 | 12/1998 |
| WO | 9510317 A1 | 4/1995 |
| WO | 2006138173 A2 | 12/2006 |
| WO | 07071436 A2 | 6/2007 |
| WO | 08070797 A2 | 6/2008 |
| WO | 10051025 A1 | 5/2010 |
| WO | 10087975 A1 | 8/2010 |
| WO | 2010127162 A1 | 11/2010 |
| WO | 2012112469 A2 | 8/2012 |
| WO | 2013166355 A1 | 11/2013 |
| WO | 2014130160 A1 | 8/2014 |

OTHER PUBLICATIONS

International Search Report and Written Opinion for Application No. PCT/US2014/054025 dated Nov. 19, 2014.
International Search Report and Written Opinion for Application No. PCT/US2014/055053 dated Nov. 24, 2014.
Ruiz, Carlos, Overview of PRE-CE Mark Transcatheter Aortic Valve Technologies, Euro PCR, May 25, 2010.

(56) References Cited

OTHER PUBLICATIONS

Quaden, Rene, et al., Percutaneous aortic valve replacement: resection before implantation, 836-840,European J. of Cardio-thoracic Surgery, 27 (2005).

* cited by examiner

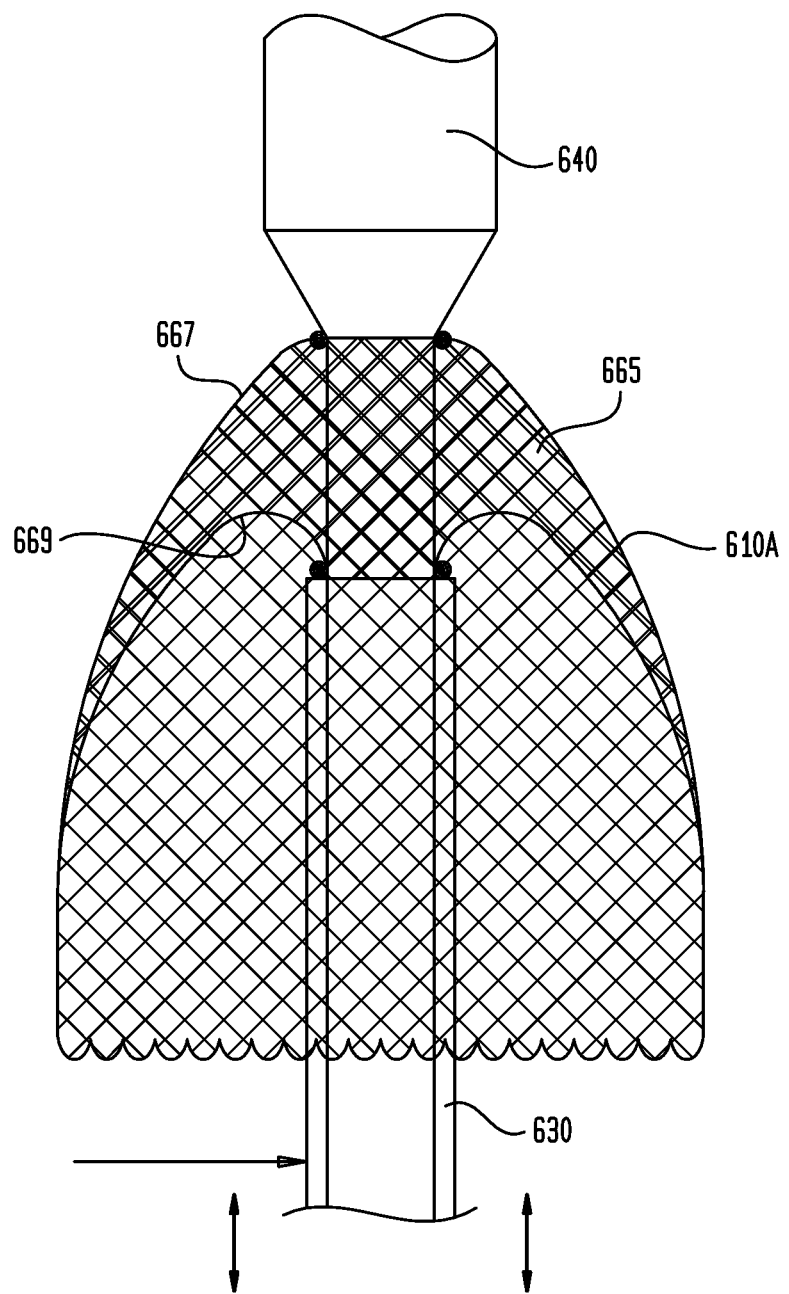

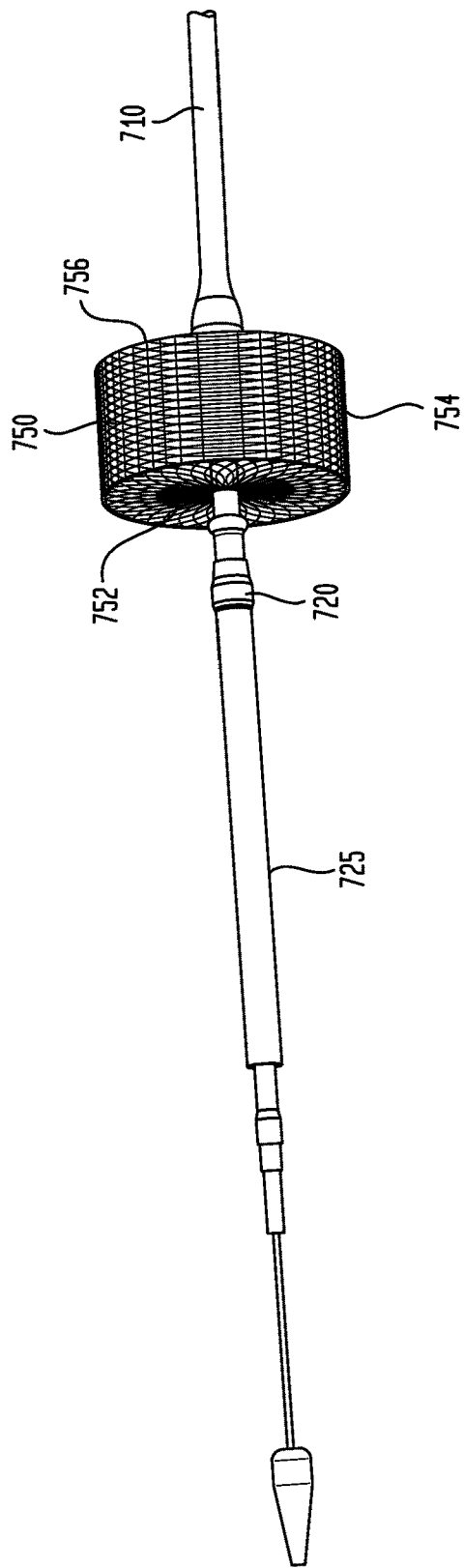

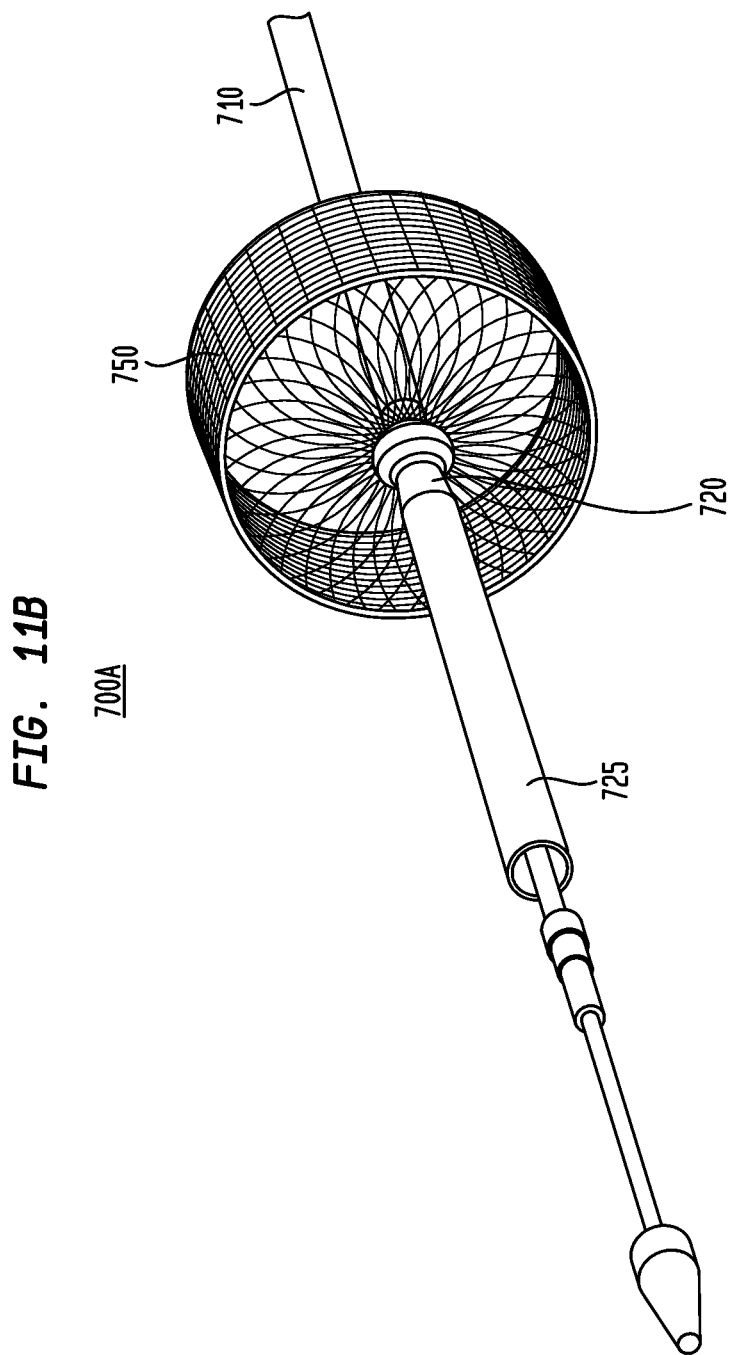

ALIGNMENT OF AN IMPLANTABLE MEDICAL DEVICE

CROSS REFERENCE TO RELATED APPLICATIONS

This application claims the benefit of the filing date of the U.S. Provisional Patent Application No. 61/877,107, filed on Sep. 12, 2013, the disclosure of which application is hereby incorporated by reference herein in its entirety.

BACKGROUND OF THE INVENTION

The present disclosure relates in general to heart valve replacement and, in particular, to collapsible prosthetic heart valves. More particularly, the present disclosure relates to devices and methods for positioning collapsible prosthetic heart valves within a native annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size.

BRIEF SUMMARY OF THE INVENTION

An embodiment according to the present disclosure includes a transcatheter valve delivery system comprising a longitudinal member extending in between a proximal end and a distal end, the longitudinal member having a compartment adjacent the distal end for holding a medical device in a collapsed condition and at least one alignment element connected to the longitudinal member. The alignment element is movable relative to the longitudinal member between a stowed position and a deployed position. In the deployed position, the alignment element is configured to urge against an anatomical surface to position the longitudinal member at a desired location relative to the anatomical surface.

Another embodiment according to the present disclosure includes a transcatheter medical device delivery system comprising a longitudinal member extending between a proximal end and a distal end, at least one alignment element associated with the longitudinal member proximal to the distal end, and an activating member associated with the longitudinal member. The longitudinal member is configured to accommodate a medical device. The activating member is configured to activate the alignment member. In the activated state, the alignment member is configured to extend radially outwardly from the longitudinal member and engage an anatomical surface in order to urge the longitudinal member into a desired position.

BRIEF DESCRIPTION OF THE DRAWINGS

Various embodiments of the present disclosure will now be described with reference to the appended drawings. It is to be appreciated that these drawings depict only some embodiments of the disclosure and are therefore not to be considered limiting of its scope.

FIG. 9C is a partial side view of the delivery system of FIG. 9A illustrating the alignment element in another expanded configuration;

FIG. 11A is a partial side view of a transcatheter valve delivery system illustrating another embodiment of an alignment element in accordance with the present disclosure; and FIG. 11B is a partial perspective view of the transcatheter valve delivery system of FIG. 11A.

DETAILED DESCRIPTION

Despite the various improvements that have been made to the collapsible prosthetic heart valve delivery process, conventional devices suffer from some shortcomings. For example, with conventional self-expanding valves, the clinical success of the valve is dependent on accurate deployment and anchoring. Inaccurate deployment and anchoring of the valve increases risks, such as those associated with valve migration. Inaccurate deployment and anchoring may also result in the leakage of blood between the implanted heart valve and the native valve annulus, commonly referred to as paravalvular leakage (also known as "perivalvular leakage"). In aortic valves, this leakage enables blood to flow from the aorta back into the left ventricle, reducing cardiac efficiency and putting a greater strain on the heart muscle.

There, therefore, is a need for further improvements to the devices, systems, and methods for positioning and collapsible prosthetic heart valves. Specifically, there is a need for further improvements to the devices, systems, and methods for accurately implanting a prosthetic heart valve. For instance, it is desirable to position the prosthetic valve precisely within the native anatomy to achieve optimal results. Furthermore, it may be desirable to reduce or minimize the effort and time spent by a user to achieve the precise positioning of the prosthetic valve. Among other advantages, the present disclosure may address one or more of these needs. More particularly, various embodiments of alignment elements may assist a user to precisely position the prosthetic valve while reducing the effort and time spent by the user.

When used in connection with devices for delivering a prosthetic heart valve or other medical device into a patient, the terms "proximal" and "distal" are to be taken as relative to the user of the delivery devices. "Proximal" is to be understood as relatively close to the user, and "distal" is to be understood as relatively farther away from the user.

Figure 1A:
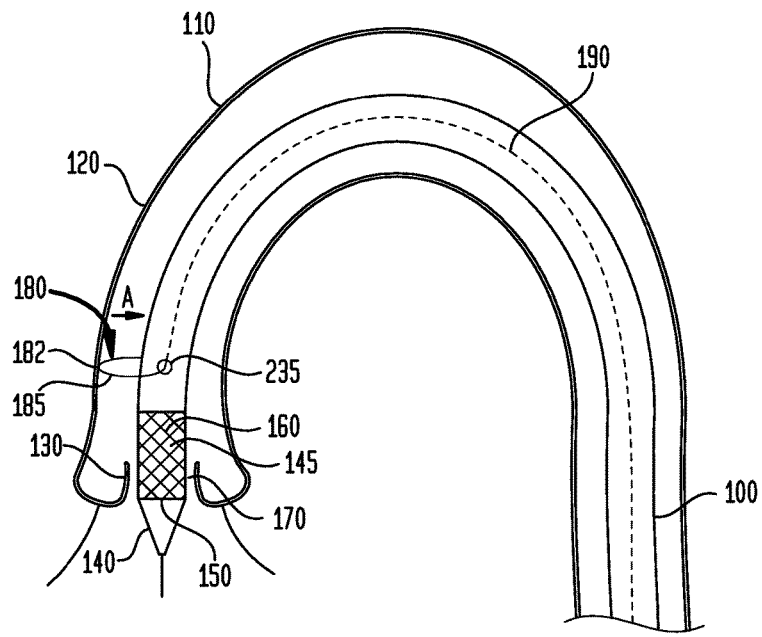
FIG. 1A is a highly schematic side view of a transcatheter valve delivery system positioned within the aortic arch and aortic valve of a patient, the delivery system including an alignment element according to one embodiment of the disclosure.
Figure 1B:
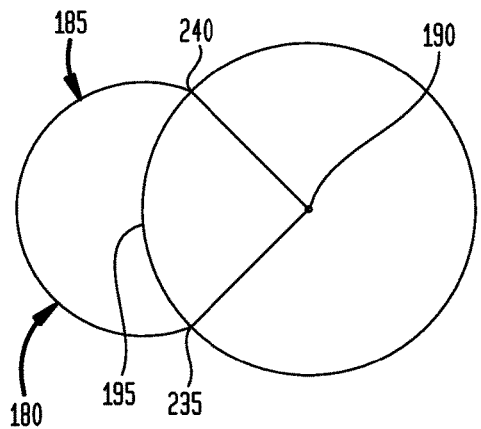
FIG. 1B is a highly schematic cross-sectional view of the alignment element shown in FIG. 1A in a deployed configuration.

Referring now to FIGS. 1A-1B, catheter 100 is schematically illustrated traversing aortic arch 110 and ascending aorta 120 to reach native aortic valve 130. Catheter 100 has a handle (not shown) connected to its proximal end (not shown) for controlling and manipulating the movements of the catheter. Catheter 100 has atraumatic tip 140 at distal end 150 thereof. Medical device 160 may be mounted at distal end 150 of catheter 100 adjacent to atraumatic tip 140, for example in compartment 145 defined adjacent to the atraumatic tip. In an exemplary embodiment, medical device 160 comprises a prosthetic heart valve having a collapsible stent. In the schematic illustration of FIG. 1A, medical device 160 is schematically illustrated as being positioned, prior to its implantation, in native aortic valve annulus 170.

Catheter 100 includes alignment element 180 projecting radially outwardly therefrom in the general vicinity of distal end 150. Alignment element 180 may be used to engage the native anatomy and guide catheter 100 to a desired coaxial position relative to native valve 130. In the illustrated embodiment, alignment element 180 may engage, at a radially outward end thereof, the native anatomy, such as sinotubular junction 182, and urge catheter 100 away from the native anatomy in a direction shown by arrow A. A user can use the handle to manipulate catheter 100 as well as alignment element 180 to enable coaxial alignment of medical device 160 with native aortic valve annulus 170, as set forth in further detail below.

Figure 1C:
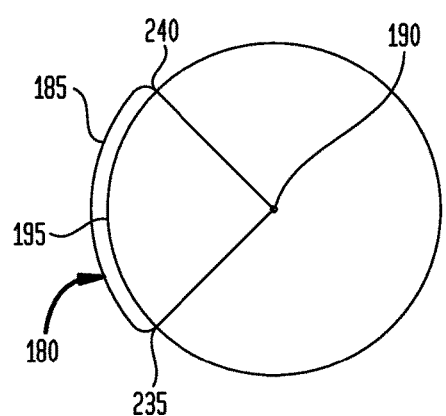
FIG. 1C is a highly schematic cross-sectional view of the alignment element shown in FIG. 1A in a stowed configuration.

Referring now to FIG. 1B, along with FIGS. 1A, 1C, alignment element 180 includes engagement loop 185 and a longitudinal stem 190. Engagement loop 185 may be formed from a biocompatible shape-memory material so that the engagement loop may be preset to a desired shape to which it will return when deployed from a compressed, stowed condition. In an exemplary embodiment, engagement loop 185 may comprise a Nitinol wire. In other embodiments, engagement loop 185 may comprise a polymer wire element. A suitable material for engagement loop 185 includes any material sufficiently flexible to be stored in the stowed configuration, yet sufficiently rigid to urge catheter 100 along with medical device 160 into a desired coaxial position in the native annulus. Engagement loop 185 and stem 190 may be formed from the same material. Alternatively, stem 190 may be formed from a more rigid material that will maintain the generally linear shape of stem 190 and provide it with sufficient columnar strength to deploy engagement loop 185.

FIG. 1B schematically illustrates alignment element 180 of FIG. 1A in a deployed configuration whereas FIG. 1C illustrates alignment element 180 of FIG. 1A in a stowed configuration. In the stowed configuration as shown in FIG. 1C, a portion of engagement loop 185 may reside within the lumen of catheter 100, with the remainder of the engagement loop pulled tightly against outer surface 195 of the catheter. As stem 190 is moved distally, for example by pushing a slide button on the catheter handle, the portion of engagement loop 185 within catheter 100 moves out therefrom through apertures 235 and 240, while the remainder of the loop moves away from outer surface 195 of the catheter. In the stowed configuration, portions of engagement loop 185 within catheter 100 are constrained by the catheter. However, as stem 190 is moved distally, the portions of engagement loop 185 emerge from catheter 100 and being freed from the constraints of the catheter, are free to revert to form the preset loop shape of the engagement loop.

As engagement loop 185 is deployed from catheter 100 by a distal movement of stem 190, the engagement loop will expand radially as it returns to its preset shape. Stem 190 and engagement loop 185 may be deployed until the engagement loop contacts the native anatomy. Thereafter, further distal movement of stem 190 causes engagement loop 185 to radially expand to an extent at least slightly greater than the radial distance between outside surface 195 of catheter 100 and the native anatomy. This further radial expansion of engagement loop 180 urges catheter 100 into coaxial alignment with aortic valve annulus 170 by pushing the catheter away from the native anatomy in the direction depicted by arrow A illustrated in FIG. 1A. It will thus be appreciated that the material of engagement loop 185 is capable of deforming for storage within catheter 100, yet possesses sufficient rigidity to maintain its radially expanded state when deployed and in contact with the native anatomy so as to urge catheter 100 away from the native anatomy.

Figure 1D:
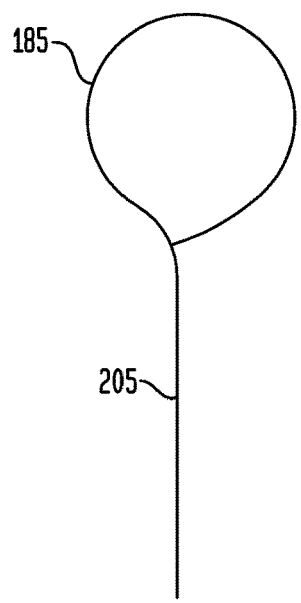
FIG. 1D is a side elevational view of one embodiment of the alignment element of FIG. 1A.
Figure 1E:
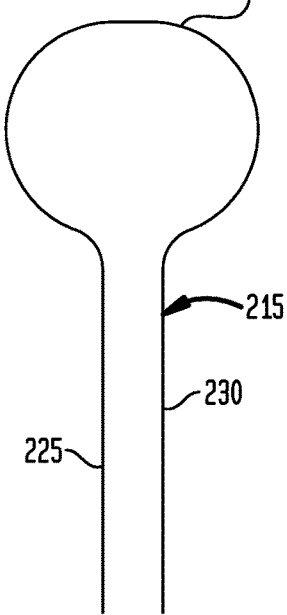
FIG. 1E is a side elevational view of another embodiment of the alignment element of FIG. 1A.

FIG. 1D schematically illustrates alignment element 180 of FIGS. 1A, 1B, and 1C. Alignment element 180 has generally longitudinal stem 190 and engagement loop 185 formed on one end of the stem. When loaded in catheter 100, longitudinal stem 190 may extend through the catheter and be connected at its proximal end to the catheter handle. At its distal end, engagement loop 185 of alignment element 180 may protrude from catheter 100 through first and second apertures 235 and 240 as shown in FIG. 1B. Longitudinal stem 190 may be manipulated by a user via the catheter handle to deploy engagement loop 185 from a stowed configuration to a deployed configuration and vice versa.

In an exemplary embodiment, engagement loop 185 may extend between about 8 millimeters (mm) and about 15 mm from the outer surface of catheter 100 when fully deployed. It will, of course, be understood that the dimensions of engagement loop 185 will depend on the dimensions of catheter 100 as well as the lumen size of the native anatomy within which the catheter is configured to operate. Once the surgical procedure has been completed, engagement loop 185 may be returned to the stowed configuration, for example, by pulling the slide button in the catheter handle. Such action will move stem 190 proximally, and pull engagement loop 185 into the lumen of catheter 100 until the engagement loop is pulled tightly against outer surface 195 of the catheter. With engagement loop 185 in the stowed configuration, catheter 100 and alignment element 180 may be removed from the patient.

In an alternate embodiment show in FIG. 1D, alignment element 212 may have generally longitudinal element 215 shaped to define engagement loop 220 and first and second stems 225, 230. The mode of operation for alignment element 212 is generally similar to that for alignment element 180 described above except that, instead of single longitudinal stem 190, first and second stems 225, 230 may be used to manipulate engagement loop 220. First and second stems 225, 230 reside within one or more lumens of catheter 100 in a fashion similar to that of stem 190 and may be connected at their proximal ends to one or more slide buttons on the catheter handle. As described above, pushing the one or more slide buttons on the catheter handle distally will cause one or both of stems 225, 230 to move distally and push engagement loop 220 out and away from catheter 100 through apertures 235, 240. Thus, distal movements of first and/or second stems 225, 230 cause engagement loop 220 to move from the stowed configuration thereof to a deployed configuration wherein engagement loop 220 may engage the native anatomy. On the other hand, proximal movements of first and/or second stems 225, 230 cause engagement loop 220 to be retracted from the deployed configuration to the stowed configuration.

Figure 2A:
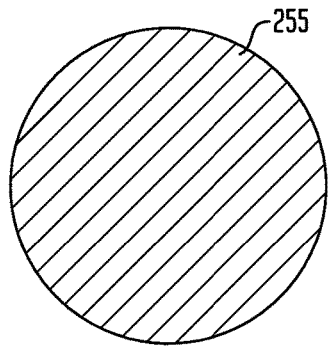
FIGS. 2A-2C are cross-sectional views of three different embodiments of a wire for forming the alignment element of FIG. 1A.
Figure 2B:
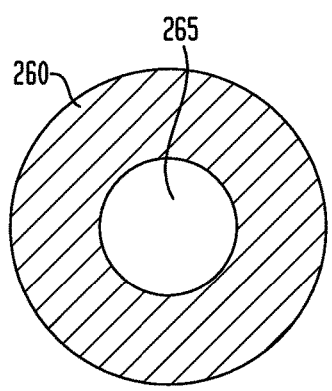
Figure 2C:
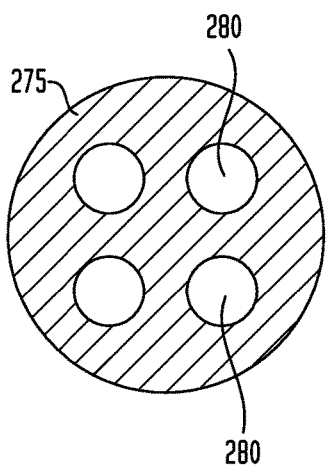

FIGS. 2A-2C show cross-sectional views through different embodiments of a wire forming the alignment element. In the embodiment illustrated in FIG. 2A, wire 255 is a monofilament having a generally solid cross-section. By way of non-limiting example only, the thickness or diameter of wire 255 may be between 0.1 millimeters (mm) and about 1 mm. In another embodiment illustrated in FIG. 2B, wire 260 has a tubular structure with lumen 265 extending therethrough. In an exemplary configuration, the outer diameter or thickness of wire 260 may be between about 0.2 mm and about 1.0 mm and the diameter of lumen 265 may be between about 0.1 mm and about 0.9 mm.

In yet another embodiment illustrated in FIG. 2C, wire 275 includes multiple lumens 280 extending therethrough. In an exemplary embodiment, the outer diameter or thickness of wire 275 may be between about 0.3 mm and about 1.0 mm, and lumens 280 may have a diameter of between about 0.1 mm and about 0.4 mm. In the illustrated embodiments, wires 255, 260, and 275 have a generally circular cross-section by way of non-limiting example only. In other embodiments, wires 255, 260, and 275, as well as lumens 265 and 280, may have cross-sections of different geometric shapes, such as oval, polygonal, square and triangular. It will further be understood that while FIG. 2C illustrates wire 275 as having four lumens 280, other embodiments may have more than four or less than four lumens extending through the wire.

Figure 3:
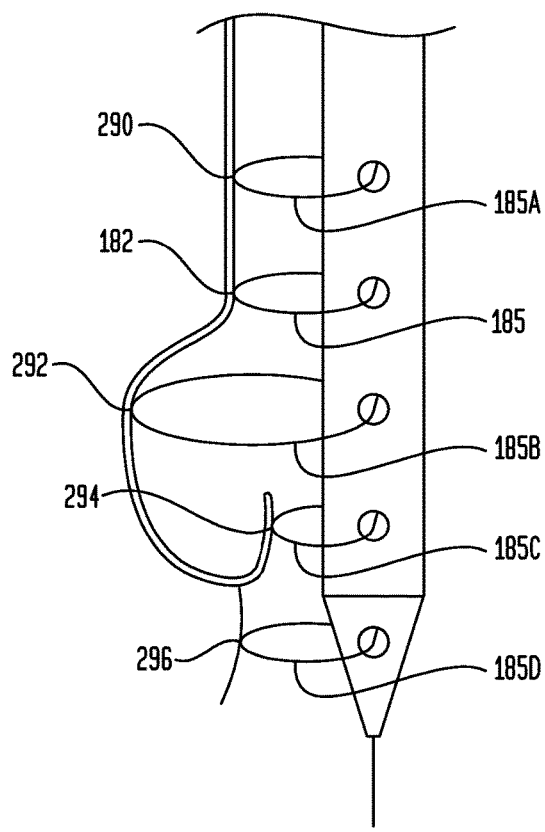
FIG. 3 is a highly schematic side view of a transcatheter valve delivery system positioned within the aortic valve of a patient, the delivery system including a plurality of alignment elements according to another embodiment of the disclosure.

While FIG. 1A illustrates engagement loop 185 urging generally against the native anatomy, such as sinotubular junction 182, FIG. 3 illustrates one or more other possible anatomical features which engaging loop 185 may engage to achieve a desired coaxial alignment of medical device 160 with aortic valve annulus 170. For instance, engagement loop 185A may engage ascending aorta wall 290, and/or engagement loop 185B may engage sinus of Valsalva 292 and/or engagement loop 185C may engage native leaflet 294 and/or engagement loop 185D may engage left ventricular outflow tract wall 296. It will therefore be appreciated that catheter 100 may include one alignment element 180 as described above, or a plurality of alignment elements, each having a similar construction to alignment element 180. When catheter 100 includes a plurality of alignment elements 180, stems 190 of the alignment elements may be bundled together so they move at the same time both proximally and distally to deploy and stow all of engagement loops 185 simultaneously. Alternatively, stems 190 may be arranged to move independently so that each engagement loop 185 may be deployed and stowed individually.

Figure 4:
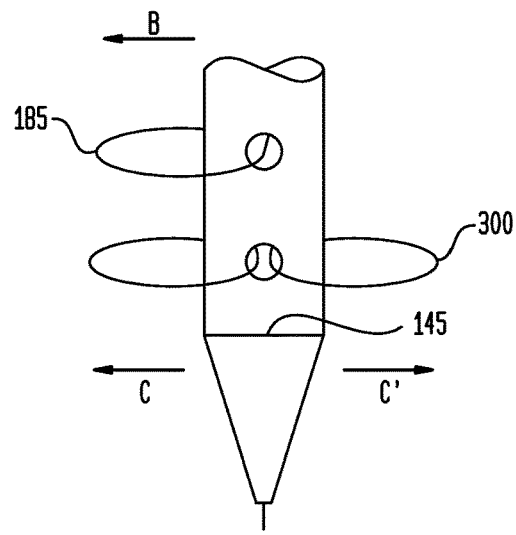
FIG. 4 is a partial side view of a transcatheter valve delivery system, the delivery system including a uni-directional alignment element and a multi-directional alignment element, according to a further embodiment of the disclosure.

Referring now to FIG. 4, two different embodiments of an engagement loop are illustrated. Uni-directional engagement loop 185 radially extends in one direction relative to catheter 100 as illustrated by arrow B, whereas bi-directional engagement loops 300 radially extend in two different directions relative to the catheter, as illustrated by arrows C, C'. While the illustrated embodiment shows bi-directional engagement loop 300 extending in two generally opposite directions, it will be understood that other embodiments may include engagement loops 300 extending in two different directions oriented at different angles. For example, bi-directional engagement loops 300 may extend in two directions generally perpendicular to one another. Still further, in another embodiment (not shown), a single engagement loop may radially extend through a very large angle, i.e., almost 360° around catheter 100. Such an embodiment is referred to herein as an omni-directional engagement loop. Engagement loops with more than two different expansion directions may be deployed and stowed by providing apertures at appropriate locations on catheter 100.

Figure 5:
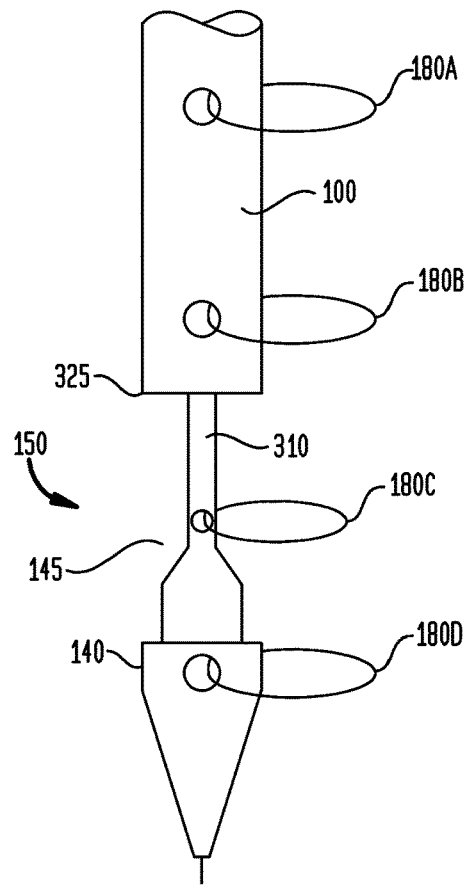
FIG. 5 is a partial side view of a transcatheter valve delivery system, the delivery system including a plurality of alignment elements, according to a still further embodiment of the disclosure.

Referring now to FIG. 5, distal end 150 of catheter 100 is illustrated in more detail. Distal end 150 of catheter 100 includes atraumatic tip 140 affixed to inner shaft 310, which is adapted to slide proximally and distally relative to catheter 100 in a telescopic fashion. A medical device, for example, a collapsible heart valve (not shown), may be assembled over inner shaft 310 just proximally of tip 140. As illustrated in FIG. 1A, compartment 145 is defined adjacent to tip 140 for accommodating the collapsible heart valve. In FIG. 4, compartment 145 is shown sheathed by catheter 100. Catheter 100 may be moved distally into abutting relationship with tip 140 (or tip 140 may be moved proximally into abutting relationship with catheter 100) to cover or sheath compartment 145 and the medical device while delivering the device to the desired location. Once at the desired location, catheter 100 may be moved proximally relative to tip 140 to expose the medical device in compartment 145 for deployment.

FIG. 5 further illustrates various sites for positioning alignment elements on catheter 100. In an exemplary embodiment, alignment element 180A may protrude from catheter 100 at a predetermined distance from distal end 325, alignment element 180B may protrude from distal end 325 of the catheter, alignment element 180C may protrude from inner shaft 310, and alignment element 180D may protrude from tip 140. Since during the deployment of the medical device, the catheter 100 may move relative to the native anatomy as well as to the medical device, whereas tip 140 and/or inner shaft 310 are more likely to be stationary relative to the native anatomy, alignment elements 180C and 180D are likely to provide better positioning assistance to the catheter. While the embodiment of FIG. 5 includes uni-directional alignment elements 180 for clarity of illustration, it will be understood that one or more of alignment elements 180 may include a uni-directional engagement loop 185 or bi-directional engagement loops 300, as illustrated in FIG. 4, or an omni-directional engagement loop.

Figure 6A:
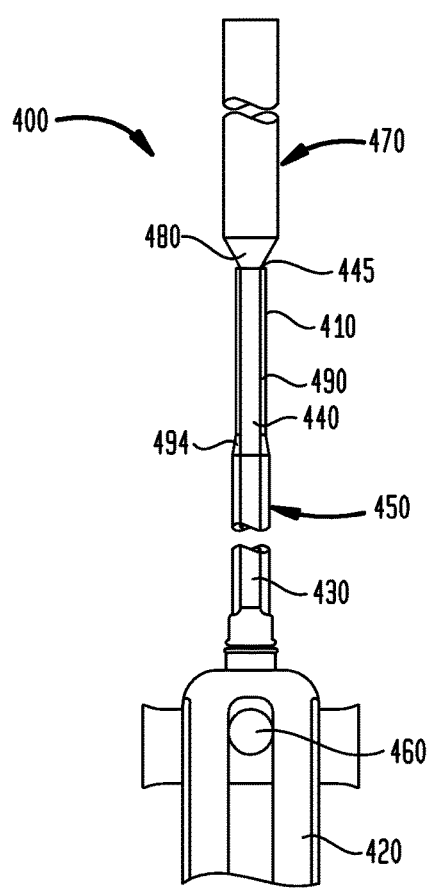
FIG. 6A is a side view of a transcatheter valve delivery system including another embodiment of an alignment element in a stowed position.
Figure 6B:
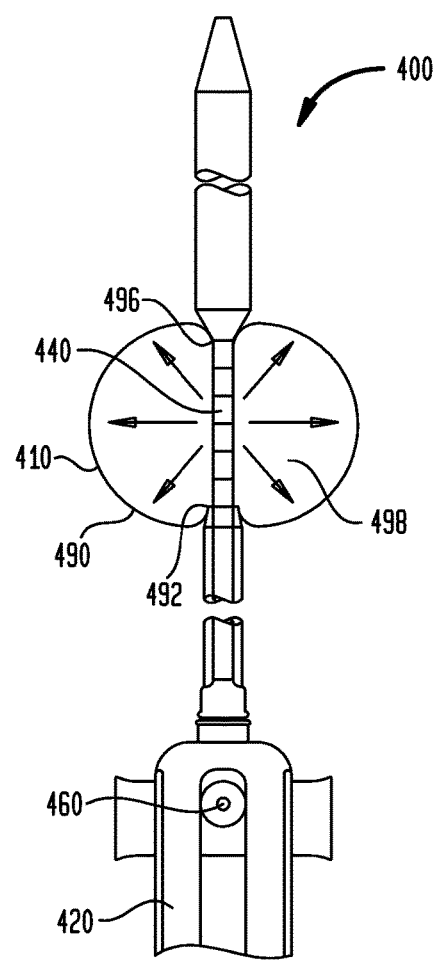
FIG. 6B is a side view of the delivery system of FIG. 6A with the alignment element in a deployed position.

Referring now to FIGS. 6A and 6B, delivery system 400 includes another embodiment of an alignment element, namely, alignment element 410. Delivery system 400 has handle 420 and catheter 430. In an exemplary embodiment, catheter 430 includes inner shaft 440 extending generally from handle 420 to distal end 445, and outer tube 450 at least partially covering inner shaft 440. Outer tube 450 is longitudinally movable relative to inner shaft 440 in a telescopic manner. In an exemplary embodiment, slide button 460 on handle 420 may be used to manipulate outer tube 450. Distal sheath 470 extends in the distal direction from distal end 445 of inner shaft 440. Distal sheath 470 may further accommodate a medical device (not shown), for example, a collapsible heart valve.

In an exemplary embodiment, distal sheath 470 is affixed to inner shaft 440 via transition member 480. More particularly, transition member 480 has a generally conical shape that tapers outwardly from distal end 445 of inner shaft 440 to distal sheath 470. An advantage of the transition member is that there are no sharp edges which could inadvertently engage native anatomy while catheter 430 traverses through, for example, an artery.

Alignment element 410 may be disposed between outer tube 450 and transition member 480. In an exemplary embodiment, alignment element 410 includes generally tubular element 490 surrounding inner shaft 440. Tubular element 490 may substantially completely surround inner shaft 440 like a sleeve. Alternatively, alignment member 410 may include one or more planar members (not shown) each partially surrounding inner shaft 440, thereby forming a tube or sleeve like structure, similar to tubular element 490. In some embodiments, one or more planar members (not shown) may be generally adjacent to one another about the circumference of inner shaft 440; in other embodiments, one or more planar members (not shown) may be spaced apart from one another about the circumference of inner shaft 440 forming a tube like structure with longitudinal slits defined in the structure.

Alignment element 410 may be secured at first end 492 to distal end 494 of outer tube 450 and at second end 496 to transition member 480. In a stowed configuration, alignment element 410 is pulled tightly against inner shaft 440, as illustrated in FIG. 6A. Alignment element 410 may be made of a polymer, such as nylon and a block copolymer such as polyether block amide, and may have a length between about 10 mm and about 100 mm, a breadth between about 5 mm and about 30 mm, and a thickness between about 0.1 mm and about 1 mm.

Now referring to FIG. 6B, when outer tube 450 is moved distally through the activation of slide button 460, its distal end 494 moves distally along with first end 492 of alignment element 410. Since second end 496 of alignment element 410 is secured to transition member 480 and remains generally stationary, the distal movement of outer tube 450 causes alignment element 410 to flex outwardly or expand away from inner shaft 440, as illustrated in FIG. 6B. Alignment element 410 may be expanded to a predetermined extent to engage native anatomy and push inner shaft 440, and with it catheter 430 and the associated medical device (not shown), into a desired coaxial position relative to the native valve annulus. In an exemplary embodiment, the extent of the expansion of alignment element 410 may be proportional to the longitudinal movement of outer tube 450, i.e., the more the outer tube 450 moves, the more the alignment element expands and vice versa.

In one configuration, inner shaft 440 may further include inflation lumens (not shown) for introducing a fluid from outside the patient's body into space 498 defined between inner shaft 440 and alignment element 410 for further assisting and/or controlling the expansion of alignment element 410, if alignment element 410 completely surrounds inner shaft 440 and connections of the alignment element and ends 492 and 496 are substantially impermeable to the inflation fluid. For instance, while outer tube 450 is being urged distally to expand alignment element 410 radially, a fluid may be introduced through the inflation lumens to cause alignment element 410 to flex outwardly relative to inner shaft 440.

Referring now to FIGS. 7A-7G, another embodiment of a delivery system is illustrated. Delivery system 500 includes longitudinal catheter 510 having proximal outer shaft 515 and distal outer tube 520. Distal outer tube 520 may include a compartment (not shown) for holding a medical device, for example, a collapsible prosthetic heart valve. A handle (not shown) may be provided at a proximal end of proximal outer shaft 515 to manipulate one or more components of distal outer tube 520 to, for example, deploy the medical device held in the distal outer tube. A plurality of lumens 525 extends through proximal outer shaft 515, each having fluid line 530 coupled thereto. At distal end 535 of each fluid line 530 is inflatable element 540. Inflatable elements 540 may be inflated by a suitable fluid, such as, for example, Saline, carbon dioxide, and iodine-based contrast media In a natural or relaxed configuration, inflatable elements 540 have sizes substantially similar to fluid lines 530. In an inflated or expanded configuration, however, inflatable elements 540 expand in a balloon-like fashion to assume sizes multiple times that those fluid lines 530.

Figure 7A:
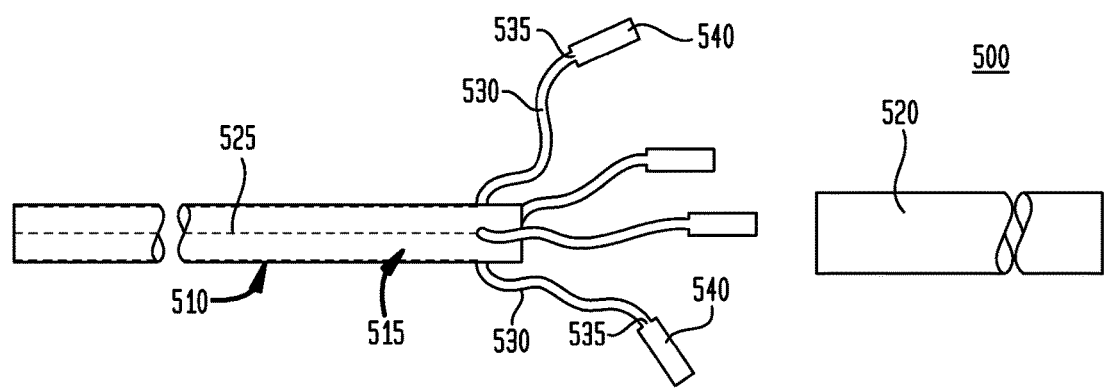
FIG. 7A is a side view of a transcatheter valve delivery system, the delivery system including a plurality of alignment elements attached to a proximal outer member according to an embodiment of the disclosure.
Figure 7B:
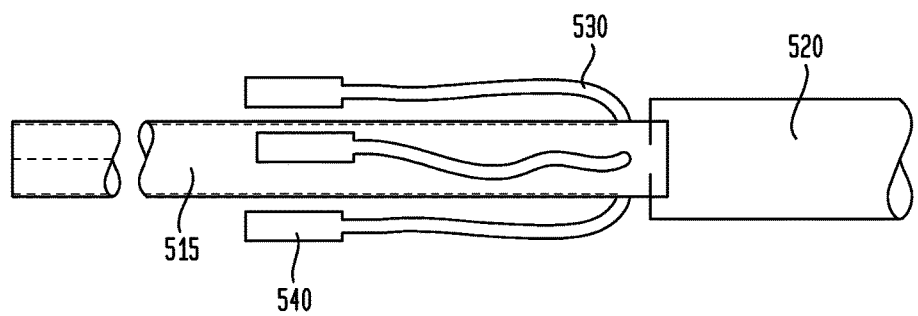
FIG. 7B is a side view of the delivery system of FIG. 7A illustrating the coupling of a distal outer tube to a proximal inner shaft.
Figure 7C:
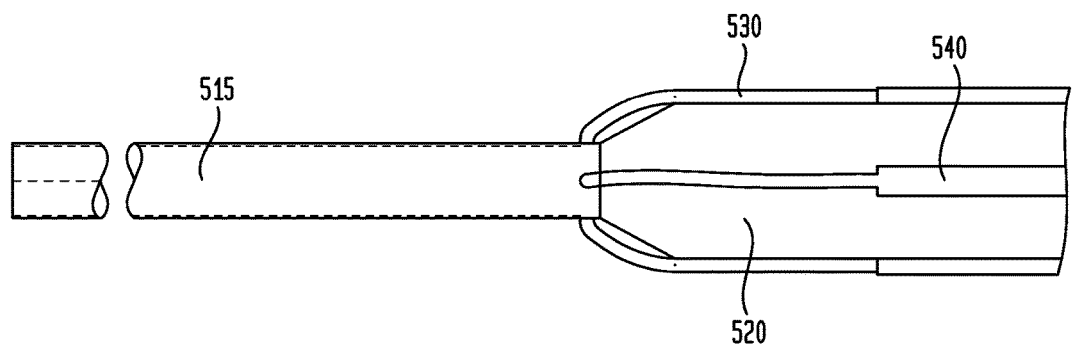
FIG. 7C is a side view of the delivery system of FIG. 7A illustrating the plurality of alignment elements overlying the distal outer tube.

As illustrated in FIG. 7B, distal outer tube 520 may be securely coupled to proximal outer shaft 515. Fluid lines 530 and associated inflatable elements 540 are schematically illustrated as pulled proximally to facilitate coupling of distal outer 520 to distal outer shaft 515. FIG. 7C, on the other hand, illustrates that when outer tube 520 is coupled to outer shaft 515, fluid lines 530 and inflatable elements 540 may be so positioned as to overlie outer tube 520. While the illustrated embodiments depict fluid lines 530 of generally equal length, fluid lines 530 may have different lengths, depending on the requirements of a given application. In an alternative embodiment, fluid lines 530 may be dispensed with and inflatable elements 540 may be directly coupled to one or both of outer shaft 515 and outer tube 520.

Figure 7D:
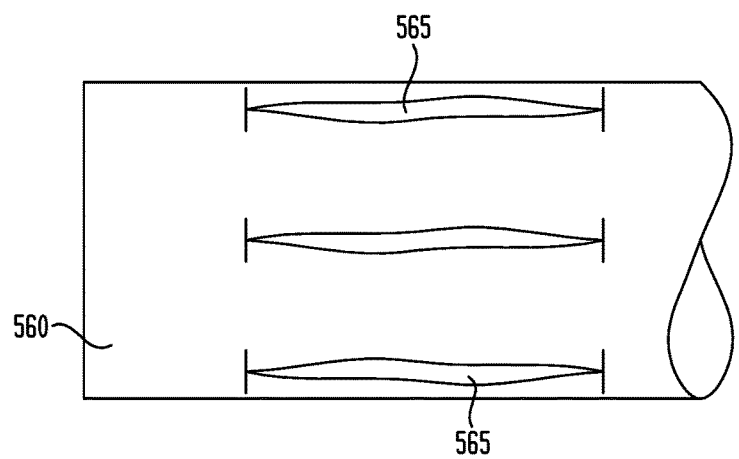
FIG. 7D is a side view of an overlay sleeve configured to overlie the plurality of alignment elements of FIG. 7A.

Delivery system 500 further includes overlay sleeve 550 configured to be mounted to distal outer tube 520, as illustrated in FIG. 7D. Overlay sleeve 550 may have a generally cylindrical body 560 with a plurality of slits 565 configured to accommodate inflatable elements 540. In an exemplary embodiment, slits 565 may secure inflatable elements 540 such that, when uninflated, inflatable elements 540 are generally held between distal outer tube 520 and overlay sleeve 550 without significantly protruding from the slits. However, once inflated, the inflatable elements 540 expand and protrude outwardly through corresponding slits 565 and radially away from overlay sleeve 550.

In an exemplary embodiment, proximal outer shaft 515 may be made of a copolymer such as polyether block amide, fluid lines 530 may be made of a polymer such as polyether block amid and inflatable elements 540 may be made of a polymer such as polyether block amide. Also, overlay sleeve 550 may be made of a material such as nylon and polyether block amide.

Figure 7E:
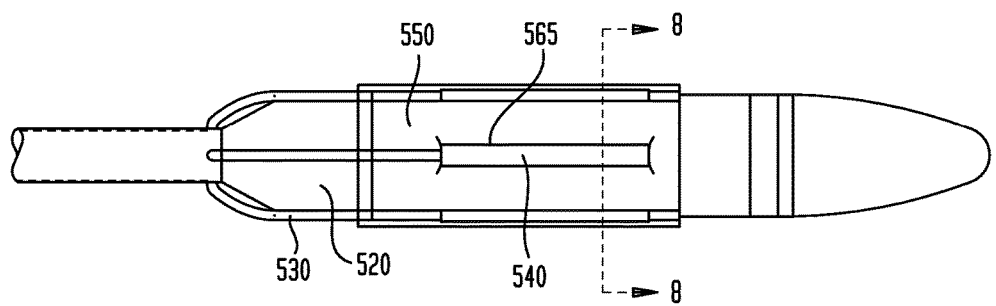
FIG. 7E is a side view of the overlay sleeve of FIG. 7D mounted to the delivery system of FIG. 7A.

In the illustrated embodiment, delivery system 500 includes four fluid lines 530, each with inflatable element 540, coupled to four lumens 525. It will, of course, be understood that other embodiments of delivery system 500 may include a different number of lumens 525, fluid lines 530, inflatable elements 540 and slits 565 in overlay element 550, depending on the requirements of a given application. Slits 565 in overlay sleeve 550 may be generally aligned with one another circumferentially or, in other embodiments, depending on the lengths of fluid lines 530 and the dimensions of inflatable elements 540, slits 565 may have different dimensions and may be aligned accordingly to accommodate the inflatable elements. FIG. 7E illustrates overlay sleeve 550 mounted to distal outer tube 520 and generally covering fluid lines 530 and accommodating inflatable elements 540 in slits 565. Overlay sleeve 550 serves to hold inflatable elements 540 against distal outer tube 520 when uninflated, while slits 565 enable inflatable elements 540 to expand outwardly and away from the distal outer tube and the overlay sleeve when inflated.

Figure 7F:
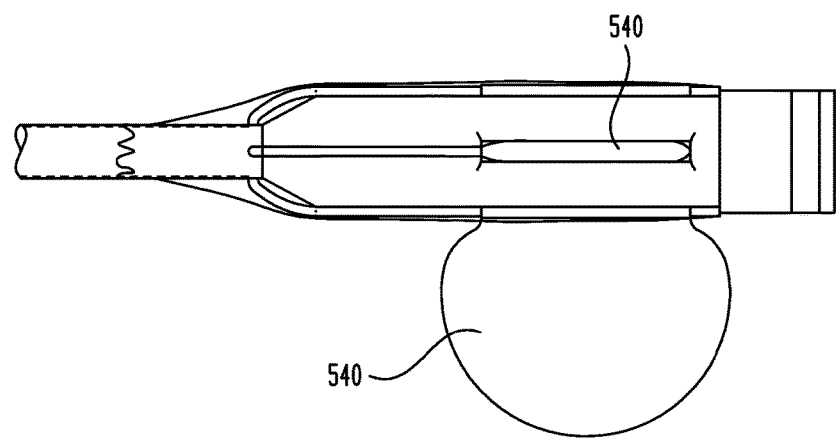
FIG. 7F is a side view of the delivery system of FIG. 7A illustrating one of the alignment elements in an expanded configuration.

As illustrated in FIG. 7F, one or more inflatable elements 540 may be inflated by selectively introducing a fluid through corresponding lumen 525 and fluid line 530. Upon inflation, inflatable element 540 protrudes outwardly from corresponding slit 565 and away from overlay sleeve 550, and may engage the native anatomy to urge the delivery system into a desired coaxial position relative to the native valve annulus.

Figure 8A:
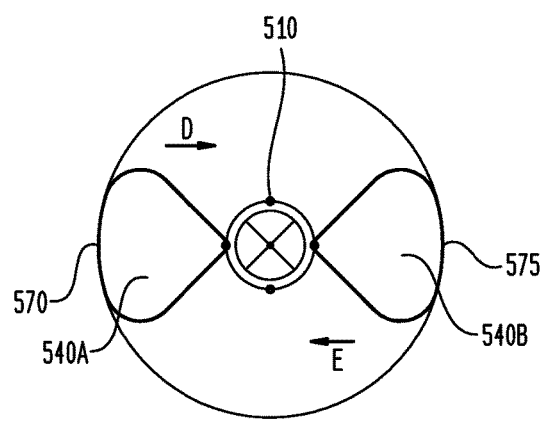
FIGS. 8A-8D are schematic cross-sections showing one or more alignment elements of FIG. 7A deployed in the aortic valve to align the delivery system relative to a patient's anatomy.
Figure 8B:
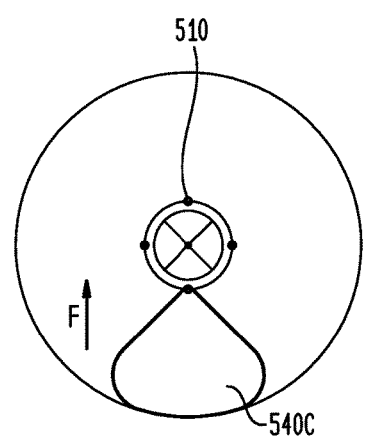
Figure 8C:
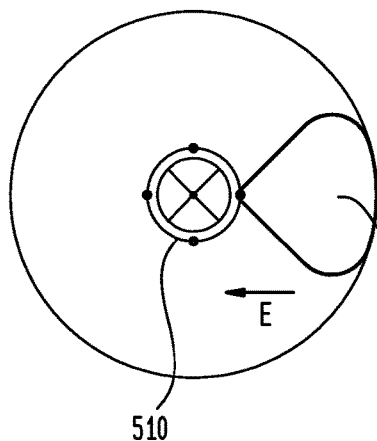
Figure 8D:
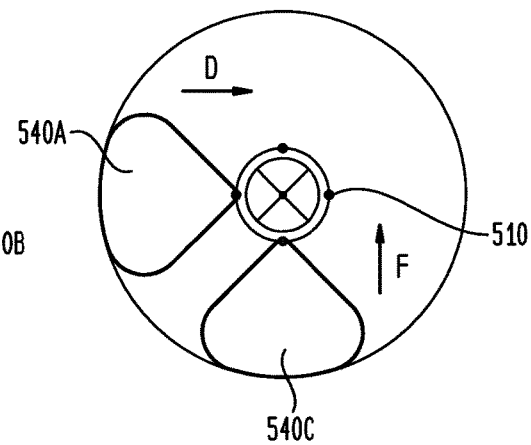

FIGS. 8A-8D are cross-sectional views through delivery system 500 depicted in FIG. 7E by line 8-8 and the native valve annulus, depicting the deployment of one or more inflatable elements 540 to achieve a desired position of longitudinal catheter 510 and the associated medical device. For instance, as shown in FIG. 8A, one inflatable element 540A may be inflated to engage the native anatomy, for example, an aortic wall, at position 570 to push catheter 510 in the direction of arrow D away from the wall. The positioning may be fine-tuned by inflating counter-acting inflatable element 540B to engage the native anatomy at position 575 to push catheter 510 in the opposite direction shown by arrow E. FIG. 8B illustrates the inflation of inflatable element 540C to push catheter 510 in the direction indicated by arrow F to achieve the desired positioning of the catheter and the associated medical device relative to the native anatomy. Likewise, FIG. 8C illustrates the inflation of inflatable element 540B to push catheter 510 in the direction indicated by arrow E to achieved the desired positioning of the catheter and the associated medical device relative to the native anatomy. While in the configuration illustrated in FIG. 8A, two counteracting inflatable elements 540A and 540B are illustrated, in FIGS. 8B and 8C only one inflatable element 540C and 540B, respectively, are illustrated as urging catheter 510 into a desired position relative to the native anatomy. Finally, FIG. 8D illustrates the selective inflation of adjacent inflatable elements 540A and 540C to push catheter 510 in the directions indicated by arrows D and F, respectively, to achieve the desired positioning of catheter 510 and the associated medical device. While in the illustrations of FIGS. 8A-8D, inflatable elements 540A, 540B, and 540C are schematically illustrated as being similar to one another, it will be appreciated that in other embodiments, the inflatable elements may either be sized differently or inflated differently from one another to achieve the desired position of the catheter and the associated medical device.

Referring now to FIGS. 9A-9D, portions of catheter 600 of a delivery device including embodiments of another alignment element 610 are illustrated. Catheter 600 includes inner shaft 620, movable proximal sheath 630 and distal sheath 640. A medical device, for example, a prosthetic collapsible heart valve, may be held in a compartment covered by distal sheath 640. Alignment element 610 is disposed circumferentially about inner shaft 620. Alignment element 610 may be in the form of a braided tube 642, which may substantially or completely surround inner member 620 like a sleeve. In an alternative arrangement illustrated in FIG. 9D, alignment member 610 may include one or more longitudinal segments 643 of a braided tube, each partially surrounding inner shaft 620 and together forming a tube or sleeve like configuration. These segments 643 of a braided tube may be generally adjacent to one other, or one or more of these segments may be spaced apart from one another about inner shaft 620.

Braided tube 642 may be securely coupled at a first end 650 to distal end 645 of proximal sheath 630, and at a second end 660 to transition member 655 of distal sheath 640. In an exemplary embodiment, braided tube 642 may have a length between about 20 mm and about 200 mm, a diameter between about 4 mm and about 30 mm and a thickness between about 0.1 mm and about 1.0 mm.

Figure 9A:
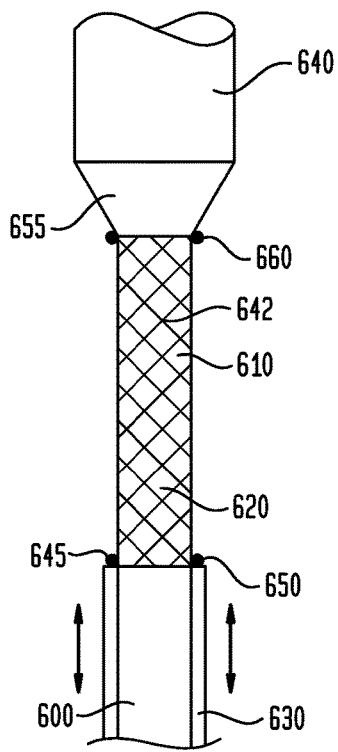
FIG. 9A is a partial side view of a transcatheter valve delivery system, the delivery system including still another embodiment of an alignment element according to an embodiment of the disclosure.
Figure 9B:
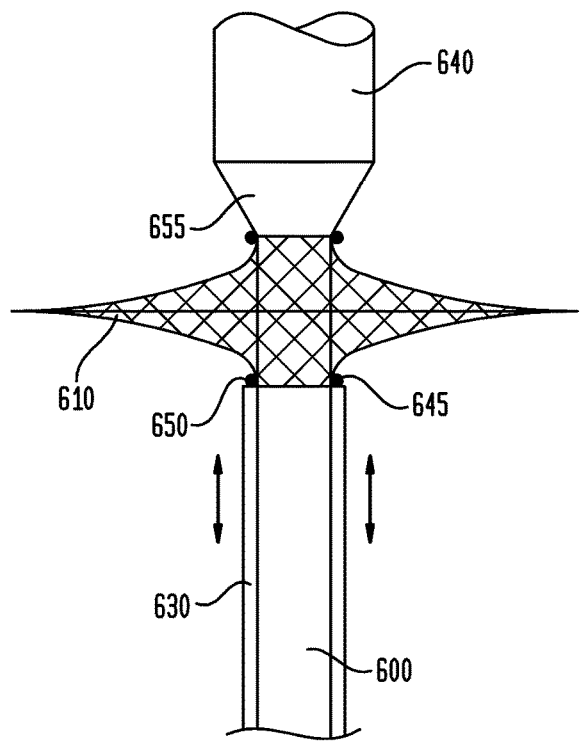
FIG. 9B is a partial side view of the delivery system of FIG. 9A illustrating the alignment element in an expanded configuration.
Figure 9D:
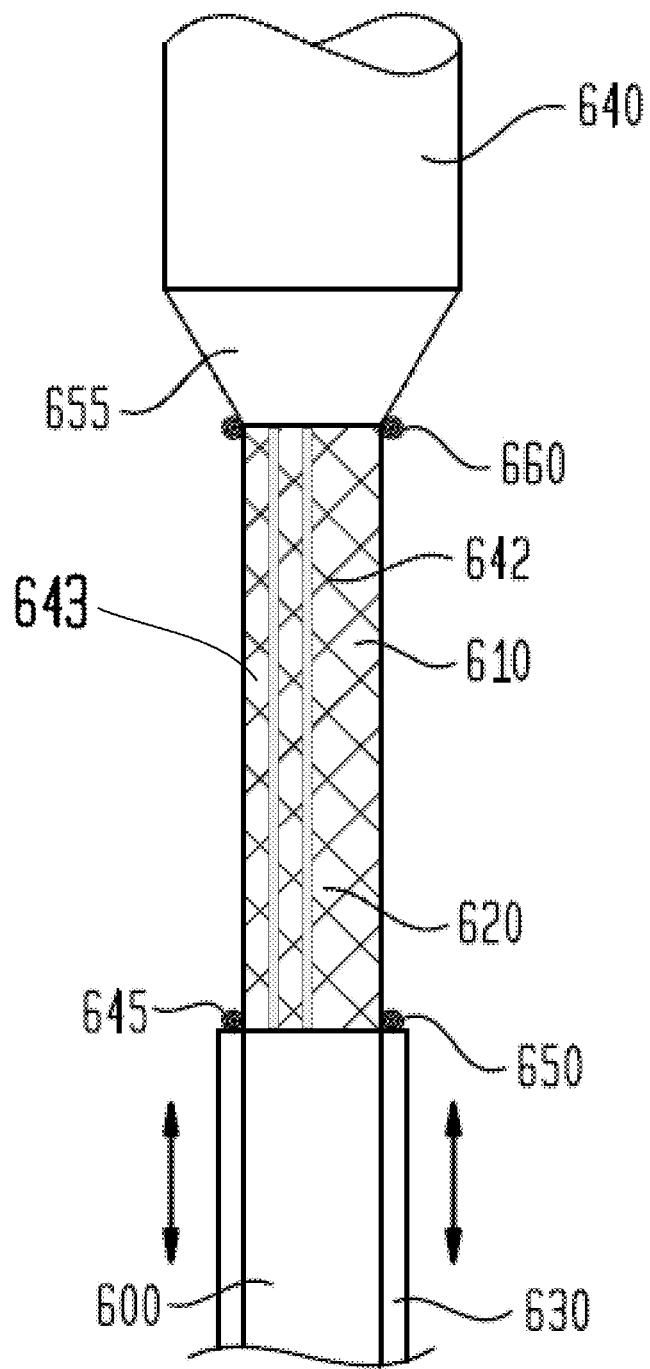
FIG. 9D is a partial side view of a transcatheter valve delivery system, the delivery system including still another embodiment of an alignment element according to an embodiment of the disclosure.

Braided tube 642 may be made from wires of a biocompatible material, including a shape memory metal such as Nitinol, or a polymer such as Polyether ether ketone (PEEK) and para-aramid synthetic fibers, for example, available under the trademark KEVLAR®. When proximal sheath 630 is pushed distally while holding distal sheath 640 in place, braided tube 642 collapses longitudinally and expands radially outward relative to catheter 600 and assumes a deployed configuration, as illustrated in FIG. 9B. On the other hand, when proximal sheath 630 is pulled proximally while holding distal sheath 640 in place, braided tube 642 expands longitudinally and contracts radially until it ultimately reaches a stowed configuration in which it closely encircles inner shaft 620, as illustrated in FIG. 9A. It will be appreciated that the extent of longitudinal movement of proximal sheath 630 relative to distal sheath 640 controls the extent of radial expansion of braided tube 642. Thus, the longer the longitudinal movement of proximal sheath, the more the radial expansion of braided tube 642 and vice versa. Alignment element 610 may be configured to assume different shapes in the deployed configuration. When in the form of braided tube 642 secured at both ends, alignment element 610 may form a generally disc-like structure, as illustrated in FIG. 9B.

In another embodiment, alignment element 610A may define a mushroom-like structure, as illustrated in FIG. 9C. More particularly, FIG. 9C illustrates a deployed configuration wherein alignment element 610A defines mushroom head 665. Alignment element 610A may include first segment 667 proximal to distal sheath 640 and second segment 669 proximal to proximal sheath 630. In this embodiment, alignment element 610 is braided from shape-memory wires configured to assume a mushroom head shape when free of any external constraints. More particularly, as proximal sheath 630 moves longitudinally toward generally stationary distal sheath 640, second segment 669 begins to fold over proximally over proximal sheath 630 in an inwardly manner. At the same time, first segment 667 is pulled proximally by second segment 669 thereby forming a cap like structure over proximal sheath 630 and emulating a mushroom. In the stowed state, similar to one illustrated in FIG. 9A, however, when proximal sheath 630 and distal sheath 640 are spaced apart longitudinally, alignment element 610A assumes a tubular shape defining its stowed configuration. In all deployed configurations, alignment element 610 and alignment element 610A radially expand relative to catheter 600 and thus are capable of engaging the native anatomy and urging catheter 600 into a desired axial position.

FIGS. 10A-10D illustrate, in perspective views, different stages of deployment of alignment element 715 in a delivery system 700. Delivery system 700 includes proximal outer sheath 710, alignment element 715, transition member 720, distal outer sheath 725 and atraumatic tip 730. A medical device, for example, a prosthetic collapsible heart valve (not shown), may be stored within a compartment covered by distal outer sheath 725 and adjacent to atraumatic tip 730. Alignment element 715 may be in the form of a braided tube substantially surrounding an inner sheath (not shown) between proximal outer sheath 710 and transition member 720, and may include proximal segment 735, intermediate segment 740 and distal segment 745. Proximal segment 735 is connected to proximal outer sheath 710 whereas distal segment 745 is connected to transition member 720. Intermediate segment 740 may be connected to an inner shaft (not shown) extending between proximal outer sheath 710 and distal outer sheath 725. Intermediate segment 740 may be constrained, for example, by the inner shaft to resist any radial expansion relative to the inner shaft. Such a configuration for intermediate segment 740 may be achieved, for example, by heat setting braided tube to resist any radial expansion along the intermediate segment.

Figure 10A:
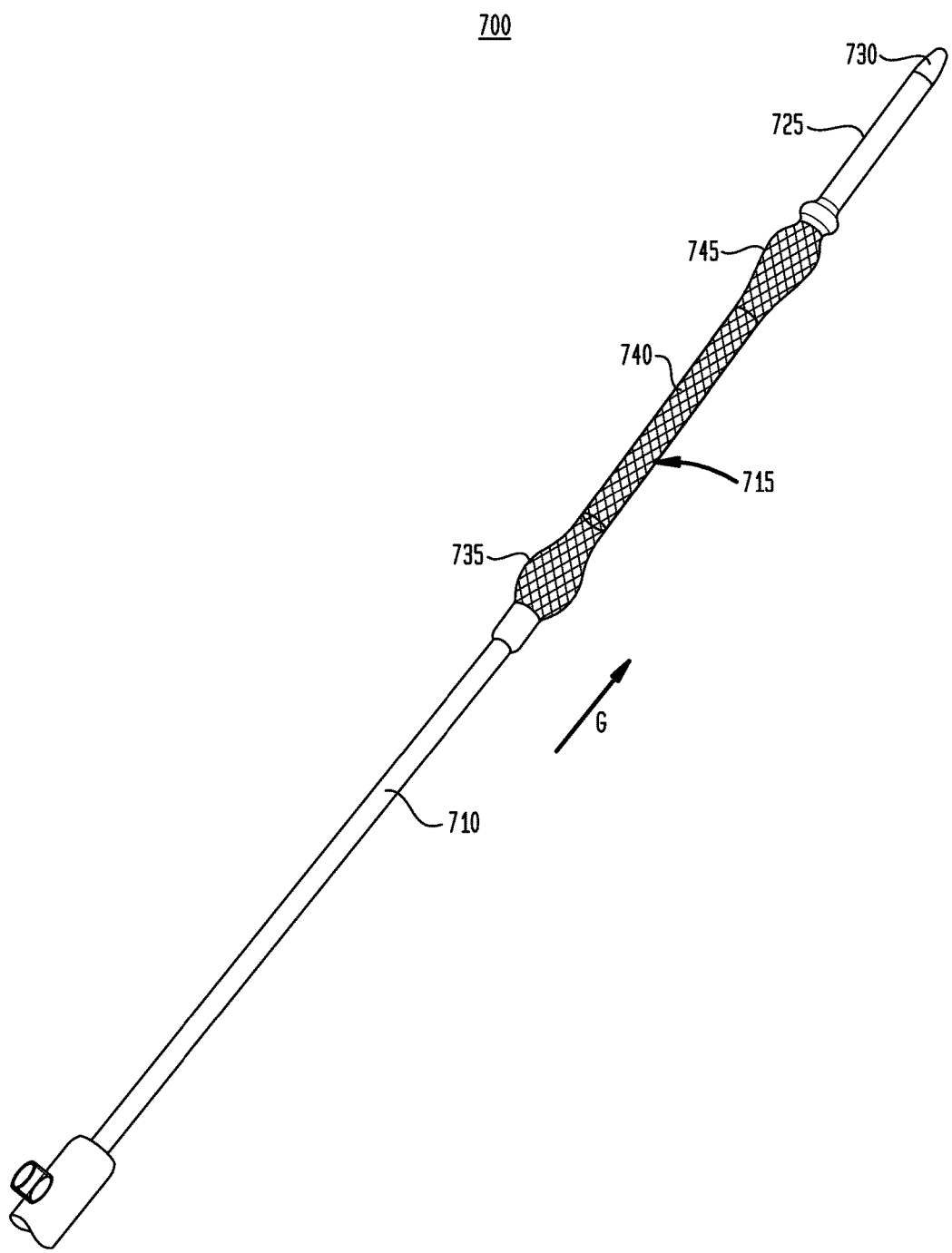
FIGS. 10A-10D illustrate various steps for deployment of an alignment element of a delivery system in accordance with the present disclosure.

FIG. 10A illustrates an initial stage of deployment of alignment element 715, during which proximal outer sheath 710 is moved distally in the direction shown by arrow G while keeping distal outer sheath 725 generally stationary. As the distance between proximal outer sheath 710 and distal outer sheath 725 lessens, proximal segment 735 and distal segment 745 begin to bulge radially outwardly while collapsing longitudinally. Intermediate segment 740, on the other hand, collapses longitudinally without expanding radially. Thus, intermediate segment 740 tends to fit closely to the inner sheath, whether in a stowed configuration or in a deployed configuration.

Figure 10B:
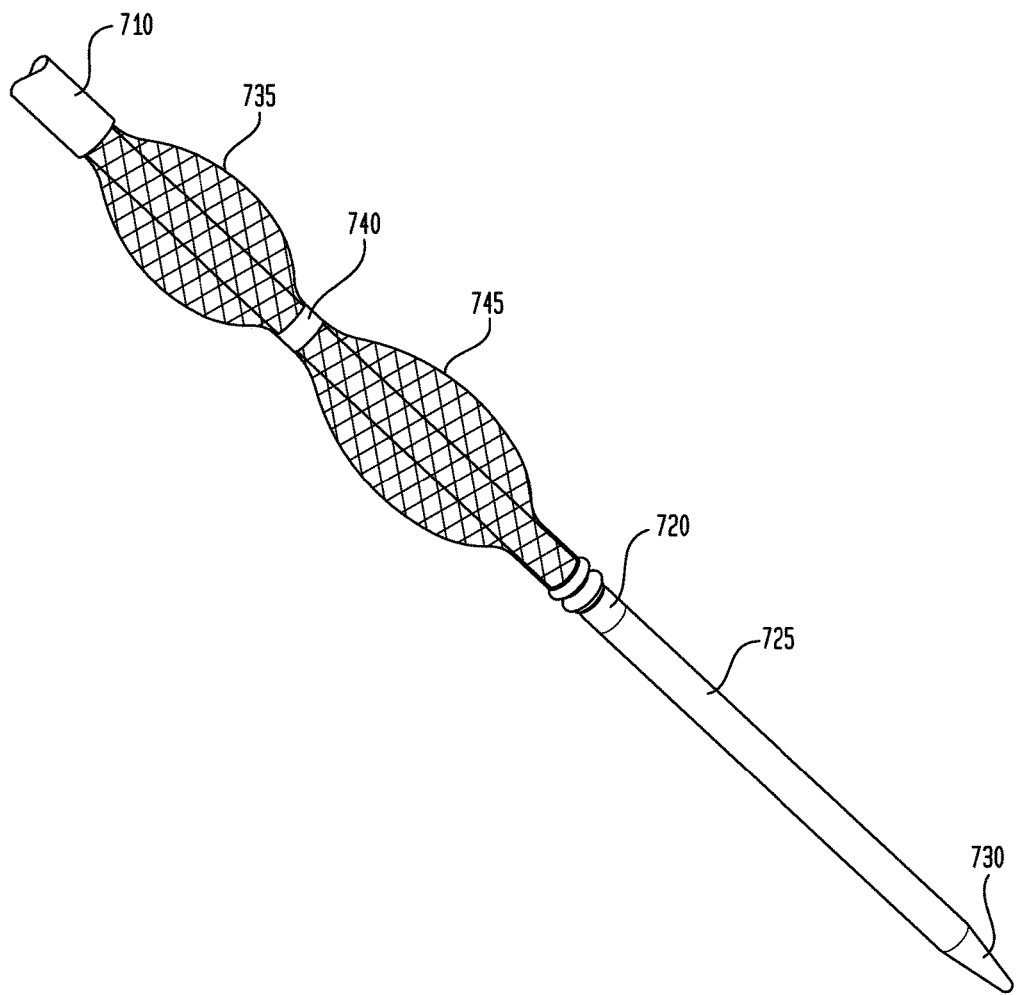
Figure 10C:
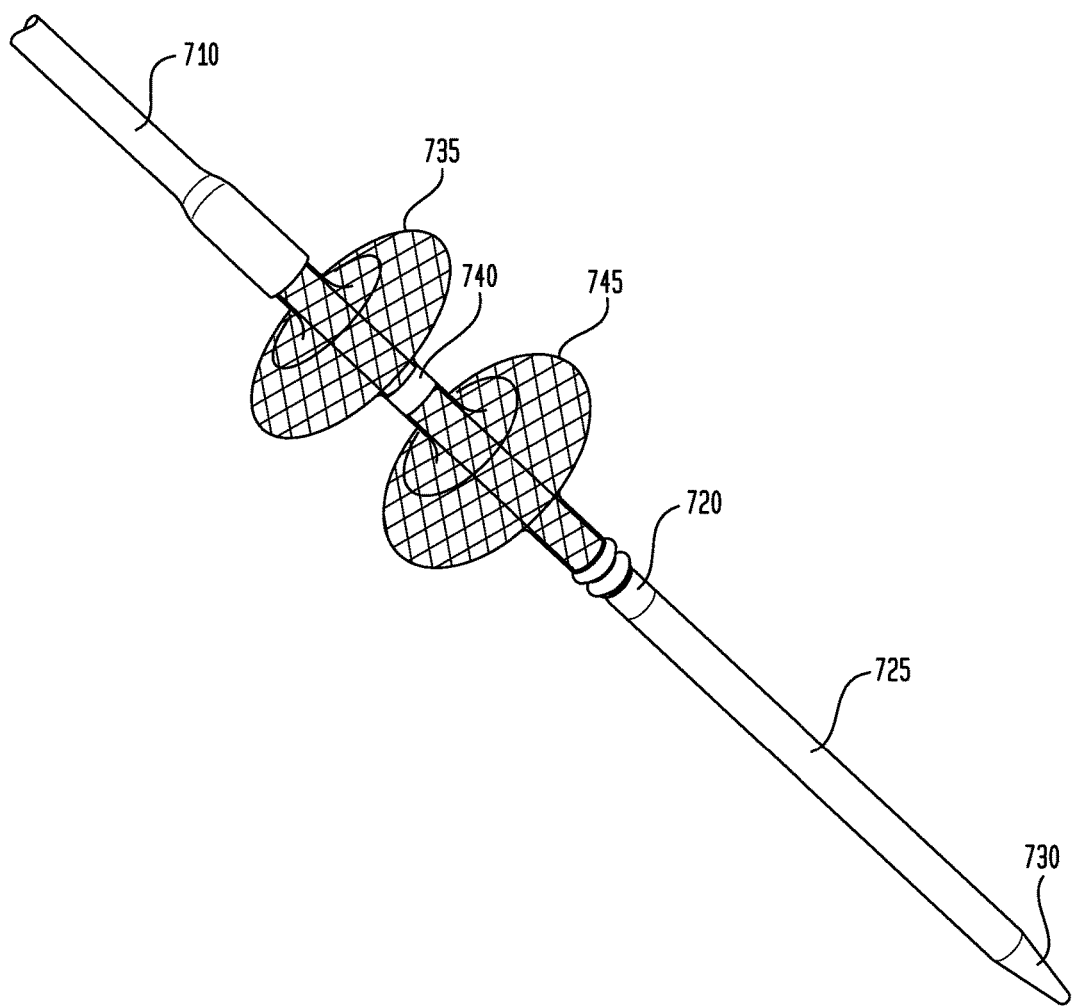

FIG. 10B illustrates a subsequent stage of deployment resulting from further distal movement of proximal outer sheath 710. In this stage, proximal segment 735 and distal segment 745 are bulged further outwardly, defining a valley therebetween along intermediate segment 740. As the deployment of alignment element 715 progresses with further distal movement of proximal outer sheath 710 relative to distal outer sheath 725, proximal segment 735 and distal segment 745 bulge even further outwardly and begin to take their disc-like shapes and intermediate segment 740 collapses further longitudinally, as illustrated in FIG. 10C.

Figure 10D:
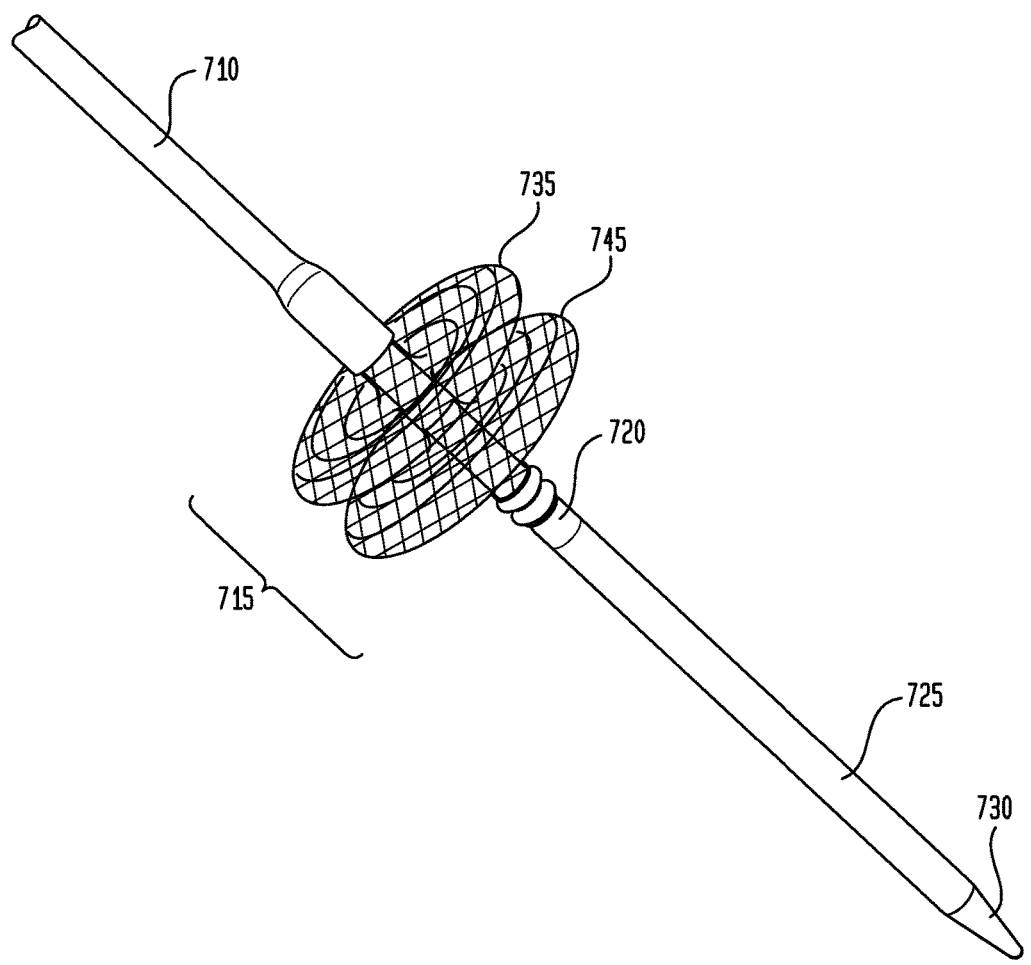

Finally, FIG. 10D illustrates alignment element 715 in a fully deployed configuration, wherein proximal segment 735 and distal segment 745 assume their disc-like shape and are generally adjacent to one another spaced apart only by shortened intermediate segment 740. In the fully deployed configuration, proximal segment 735 and distal segment 745, which extend radially outward relative to delivery system 700, are available to engage the native anatomy and assist in achieving a desired axial position of the delivery system and its associated medical device in, for example, the annulus of the native valve. While in the illustrated embodiment, proximal segment 735 and distal segment 745 are shown generally identical to one another in their deployed configurations, in other embodiments, proximal segment 735 and distal segment 745 may have different geometric configurations from one another. Once the medical device has been implanted, proximal outer sheath 710 may be moved proximally, and away from transition member 720. As the distance between proximal outer sheath 710 and transition member 720 increases, proximal segment 735 and distal segment 745 begin to collapse radially and extend longitudinally until they revert to their stowed configuration.

FIG. 11A is a side view of delivery system 700A with another embodiment of alignment element 750 in a deployed configuration, while FIG. 11B is a partial perspective view of delivery system 700A with alignment element 750 in the deployed configuration. While the elements of delivery system 700A of FIG. 11A are generally similar to those of delivery system 700 of FIGS. 10A-10D described above, alignment element 750 assumes a different shape in its deployed configuration as compared to alignment element 715. Rather than forming the two-disc configuration described above, alignment element 750 forms a generally cylindrical shape. Alignment element 750 includes proximal segment 752, intermediate segment 754 and distal segment 756. In its stowed state, system 700A is generally similar to the stowed state of system 700 illustrated in FIG. 10A. When proximal outer sheath 710 is moved distally while keeping distal outer sheath 725 generally stationary, alignment element 750 collapses longitudinally and expands radially outward relative to proximal outer sheath 710 and distal outer sheath 725. More particularly, proximal segment 752 flares radially outwardly to form one end of a cylinder, intermediate segment 754 expands radially while contracting longitudinally to form the body of the cylinder and distal segment 756 flares radially outwardly to form another end of the cylinder, as illustrated in FIG. 11A. Alignment element 750 may be formed of wires of a shape-memory alloy such that, in the deployed configuration, the alignment element assumes the generally cylindrical shape illustrated in FIGS. 11A and 11B. Alignment element 750, when deployed to assume its cylindrical shape, engages the native anatomy and urges proximal outer sheath 710 and distal outer sheath 725, along with the associated medical device, into a desired position relative to the native anatomy.

As disclosed herein, a transcatheter valve delivery system includes a longitudinal member extending between a proximal end and a distal end, the longitudinal member having a compartment adjacent the distal end for holding a medical device in a collapsed condition; and at least one alignment element connected to the longitudinal member, the alignment element being movable relative to the longitudinal member between a stowed position, and a deployed position, the alignment element is configured to urge against an anatomical surface to position the longitudinal member at a desired location relative to the anatomical surface; and/or the longitudinal member comprises a tube with an outer wall and a lumen, the alignment element including a stem and an engagement loop at a distal end of the stem, the stem extending through the lumen and the engagement loop projecting through the outer wall of the longitudinal member; and/or the engagement loop may be formed of a wire including a shape memory material; and/or the shape memory material may be selected from the group consisting of nitinol and a polymer; and/or the alignment element may comprise a wire, the wire being selected from the group consisting of a monofilament wire, a tubular wire, and a multi-lumen wire; and/or in the deployed position of the alignment element, the engagement loop may be configured to substantially surround a circumference of the longitudinal member; and/or the delivery system may further include an atraumatic tip at the distal end of the longitudinal member, wherein the engagement loop may be mounted on the atraumatic tip; and/or the longitudinal member may include an outer tube; and an inner shaft extending through the outer tube; and wherein the alignment element may include a generally tubular element having a first end and a second end, the first end being operatively secured to the outer tube and the second end being secured to the inner shaft such that the generally tubular element substantially surrounds the inner shaft, whereby a first longitudinal movement of the outer tube relative to the inner shaft longitudinally collapses the alignment element and a second longitudinal movement of the outer tube relative to the inner shaft radially expands the alignment element; and/or the alignment element may include an inflatable element; and the longitudinal member may include a proximal inner shaft having a distal end and at least one lumen extending therethrough, the at least one lumen being in fluid communication with the inflatable element, a distal outer tube coupled to the distal end of the inner shaft, and an overlay sleeve configured to at least partially cover the distal outer tube and the inflatable element, the overlay sleeve including a slit configured to receive the inflatable element in an inflated condition such that the inflatable element protrudes through the slit and away from the overlay sleeve; and/or the longitudinal member may include a distal sheath; a proximal sheath; and an inner shaft extending through the proximal sheath, the proximal sheath being movable; longitudinally relative to the inner shaft; and the alignment element may include: a braided tube having a first end and a second end, the first end being operatively secured to the proximal sheath and the second end being operatively secured to the distal sheath such that the braided tube substantially surrounds the inner shaft, whereby a distal movement of the proximal sheath relative to the distal sheath is configured to cause a longitudinal collapse of the braided tube and a proximal movement of the proximal sheath relative to the distal sheath is configured to cause a radially outward expansion of the braided tube.

Also as disclosed herein, a transcatheter medical device delivery system includes a longitudinal member extending between a proximal end and a distal end, the longitudinal member configured to accommodate a medical device; at least one alignment element associated with the longitudinal member proximal to the distal end; and an activating member associated with the longitudinal member, the activating member configured to activate the alignment member, wherein in the activated state, the alignment member is configured to extend radially outwardly from the longitudinal member and engage an anatomical surface in order to urge the longitudinal member into a desired position; and/or the alignment member may comprise an engagement loop protruding out of the longitudinal member, and the activating member may comprise a longitudinal stem coupled to the engagement loop and extending through the longitudinal member, such that a first longitudinal movement of the activating member towards the distal end is configured to cause the engagement loop to expand radially relative to the longitudinal member and a second longitudinal movement of the activating member towards the proximal end is configured to cause the engagement loop to contract radially relative to the longitudinal member; and/or the engagement loop may be formed of a shape memory material; and/or the shape memory material may be selected from the group consisting of nitinol and a polymer; and/or in a deployed position of the alignment element, the engagement loop may substantially surround a circumference of the longitudinal member; and/or the longitudinal member may include an inner shaft, the activating member may include an outer shaft generally surrounding the inner shaft, and the alignment element may include a generally tubular element having a first end and a second end, the first end being operatively secured to the activating member and the second end being secured to the inner shaft such that the generally tubular element substantially surrounds the inner shaft, a first longitudinal movement of the activating member towards the distal end is configured to cause a radial collapse of the alignment element onto the inner shaft, and a second longitudinal movement of the activating member towards the proximal end is configured to cause a radial expansion of the alignment element relative to the inner shaft; and/or the alignment element may include an inflatable element, and the activating member may include a lumen extending through the longitudinal member and in fluid communication with the inflatable element such that a selective passage of a fluid through the lumen into the inflatable element is configured to inflate the inflatable element, thereby causing a radial expansion of the inflatable element relative to the longitudinal member; and/or the activating member may include a movable proximal sheath, and the alignment element may include a braided tube having a first end and a second end, the first end being operatively secured to the movable proximal sheath and the second end being operatively secured to the longitudinal member such that a first longitudinal movement of the movable proximal sheath is configured to cause a longitudinal collapse of the braided tube along the longitudinal member and a second longitudinal movement of the movable proximal sheath is configured to cause a radial expansion of the braided tube relative to the longitudinal member; and/or in a radially expanded state, the braided tube assumes a disc-like structure; and/or in a radially expanded state, the braided tube assumes a cylindrical shape.

Although the present disclosure herein has described particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A transcatheter valve delivery system, comprising:
a longitudinal member having a proximal end and a distal end, the longitudinal member having a compartment at the distal end for holding a medical device in a collapsed condition, the longitudinal member including:
a distal sheath covering the compartment such that the medical device is held in the compartment and is covered by the distal sheath;
a proximal sheath; and
an inner shaft extending through the proximal sheath, the proximal sheath being movable longitudinally relative to the inner shaft; and
at least one alignment element connected to the longitudinal member, the alignment element being movable relative to the longitudinal member between a stowed position and a deployed position, the alignment element including:
a braided tube having a first end and a second end, the first end being operatively secured to the proximal sheath and the second end being operatively secured to the distal sheath such that the braided tube substantially surrounds the inner shaft, whereby a distal movement of the proximal sheath towards the distal sheath is configured to cause a longitudinal collapse of the braided tube such that the braided tube forms a disc-like structure and a proximal movement of the proximal sheath away from the distal sheath is configured to cause a longitudinal expansion of the braided tube, the braided tube being made from a shape memory metal and configured to form the disc-like structure when collapsed longitudinally,
wherein in the deployed position, the alignment element is configured to urge against an anatomical surface to position the longitudinal member at a desired location relative to the anatomical surface.

2. The system of claim 1, wherein the braided tube comprises two or more longitudinal segments, each longitudinal segment partially surrounding the inner shaft.

3. The system of claim 2, wherein the longitudinal segments are adjacent to one another.

4. The system of claim 2, wherein the longitudinal segments are spaced apart from one another.

5. A transcatheter medical device delivery system comprising:
a longitudinal member having a proximal end and a distal end and including an inner shaft and a distal sheath, the longitudinal member being configured to accommodate an implantable medical device in a compartment at the distal end and covered by the distal sheath;
at least one alignment element associated with the longitudinal member proximal to the distal end; and
an activating member associated with the longitudinal member and including a proximal sheath,
wherein the at least one alignment element includes a braided tube having a first end and a second end, the first end being operatively secured to the proximal sheath and the second end being operatively secured to the distal sheath such that a first longitudinal movement of the proximal sheath is configured to cause a radial collapse of the braided tube along the longitudinal member and a second longitudinal movement of the proximal sheath is configured to cause a radial expansion of the braided tube away from the longitudinal member and to cause the expanded braided tube to engage an anatomical surface in order to urge the longitudinal member into a desired position, and
wherein the inner shaft underlying the braided tube maintains a first diameter during the radial collapse and the radial expansion of the braided tube.

* * * * *